United States Patent
Kim et al.

(10) Patent No.: US 11,771,795 B2
(45) Date of Patent: Oct. 3, 2023

(54) AIR PURIFICATION MODULE AND REFRIGERATOR COMPRISING THE SAME

(71) Applicant: SEOUL VIOSYS CO., LTD., Gyeonggi-do (KR)

(72) Inventors: Ji Won Kim, Gyeonggi-do (KR); Jae Hak Jeong, Gyeonggi-do (KR); Sang Cheol Shin, Gyeonggi-do (KR); Woong Ki Jung, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 82 days.

(21) Appl. No.: 17/072,688

(22) Filed: Oct. 16, 2020

(65) Prior Publication Data
US 2021/0030915 A1 Feb. 4, 2021

Related U.S. Application Data

(63) Continuation of application No. PCT/KR2019/004578, filed on Apr. 16, 2019.

(30) Foreign Application Priority Data

Apr. 17, 2018 (KR) ........................ 10-2018-0044391

(51) Int. Cl.
*A61L 9/20* (2006.01)
*B01D 53/00* (2006.01)
(Continued)

(52) U.S. Cl.
CPC ............ *A61L 9/205* (2013.01); *B01D 53/007* (2013.01); *B01D 53/885* (2013.01);
(Continued)

(58) Field of Classification Search
None
See application file for complete search history.

(56) References Cited

U.S. PATENT DOCUMENTS

| | | | |
|---|---|---|---|
| 7,056,476 B2 | 6/2006 | Okada et al. | |
| 2015/0033784 A1 | 2/2015 | Park et al. | |

(Continued)

FOREIGN PATENT DOCUMENTS

| | | |
|---|---|---|
| CN | 102423627 A | 4/2012 |
| CN | 103953980 A | 7/2014 |

(Continued)

OTHER PUBLICATIONS

No Name—KR101198923B1—translated document (Year: 2012).*
(Continued)

*Primary Examiner* — Jelitza M Perez
(74) *Attorney, Agent, or Firm* — Perkins Coie LLP (57) ABSTRACT

An air purification module comprises a housing having an interior space provided with an air inlet and an air outlet, and an axial type blowing fan, mounted in the housing, for moving air from the air inlet to the air outlet. The air purification module further includes an air purifying unit, provided on a flow path of the air, for purifying the air and a guide for reducing the flow rate of the air between the blowing fan and the air purifying unit. The air purifying unit includes a filter provided between the blowing fan and the air outlet and a light source unit for providing light to the filter.

18 Claims, 7 Drawing Sheets

(51) Int. Cl.
    *B01D 53/88* (2006.01)
    *F25D 17/04* (2006.01)
(52) U.S. Cl.
    CPC ........ *F25D 17/042* (2013.01); *A61L 2209/12* (2013.01); *A61L 2209/14* (2013.01); *B01D 2255/802* (2013.01); *B01D 2259/804* (2013.01); *F25D 2317/0417* (2013.01)

(56) References Cited

U.S. PATENT DOCUMENTS

2015/0064069 A1* 3/2015 Yi .............................. A61L 9/20
                                                              422/121
2019/0134251 A1* 5/2019 Jeong ...................... F25D 17/06

FOREIGN PATENT DOCUMENTS

| CN | 107062790 A | 8/2017 |
| CN | 206469578 U | 9/2017 |
| JP | 11-211209 A | 8/1999 |
| JP | 2007-125466 A | 5/2007 |
| JP | 2009-030925 A | 2/2009 |
| JP | 2015-051268 A | 3/2015 |
| KR | 1020050108828 | 11/2005 |
| KR | 100624656 | 9/2006 |
| KR | 101198923 B1 * | 11/2012 |
| KR | 1020150050022 | 5/2015 |
| KR | 1020170136896 A | 12/2017 |
| KR | 1020170141492 | 12/2017 |
| KR | 20180004979 A * | 1/2018 |
| KR | 1020180004979 | 1/2018 |
| KR | 20180004979 A * | 2/2018 |
| WO | 2016089088 A1 | 6/2016 |
| WO | 2017204934 A1 | 11/2017 |

OTHER PUBLICATIONS

International Search Report for International Application PCT/KR2019/004578, dated Jul. 31, 2019.
Examination Report issued in corresponding IN Application 202037049970, dated Apr. 18, 2022, 6 pages.
Extended European Search Report for European Application No. 19789369.6, dated Dec. 9, 2021, 8 pages.
English Translation of Office Action issued in corresponding Chinese Patent Application No. 201980003004.6, dated Jan. 11, 2023 (28 pages).
English Translation of Office Action issued in corresponding Japanese Patent Application No. 2020-557282, dated Feb. 9, 2023 (8 pages).
English Translation of Office Action from corresponding Chinese Patent Application No. 201980003004.6, dated Apr. 29, 2023 (18 pages).
Liang Rongguang, He Wenshao, et al. "Modern Automotive Air Conditioning Technology" Dec. 31, 2003, (4 pages).
Ji Shouhang "Design of Intelligent Air Purification System for Elevator Car" 2016 Special Equipment Safety and Energy Technology Series Academic Conference Proceedings Down, Dec. 31, 2017, (6 pages).

* cited by examiner

AIR PURIFICATION MODULE AND REFRIGERATOR COMPRISING THE SAME

CROSS REFERENCE TO RELATED APPLICATION

This application is a Continuation of International Patent Application No. PCT/KR2019/004578, filed on Apr. 16, 2019, and claims priority from and the benefit of Korean Patent Application No. 10-2018-0044391, filed on Apr. 17, 2018, each disclosure of which is incorporated by reference for all purposes as if fully set forth herein.

BACKGROUND

Field

Embodiments of the present disclosure relate to an air purification module and a refrigerator including the same.

Discussion of the Background

A refrigerator is a home appliance that includes a storage compartment adapted to store food in a refrigerated state and a cold air supply device adapted to supply cold air to the storage compartment to store food in a fresh state.

Among foods stored in the refrigerator, some foods have various unpleasant odors including a fishy smell or a smell of fermented foods, such as kimchi. These odors can permeate into the refrigerator and cause discomfort to a user.

The above information disclosed in this Background section is only for understanding of the background of the inventive concepts, and, therefore, it may contain information that does not constitute prior art.

SUMMARY

Embodiments of the present disclosure provide an air purification module having improved deodorization efficiency.

In accordance with one aspect of the present disclosure, an air purification module includes: a housing having an interior space defined therein and provided with an air inlet and an air outlet; an axial type blowing fan disposed inside the housing to force air to flow from the air inlet to the air outlet; an air purification unit disposed on a flow path of the air and purifying the air; and a first guide reducing a flow rate of the air between the blowing fan and the air purification unit. The air purification unit includes a filter disposed between the blowing fan and the air outlet; and a light source unit emitting light to the filter.

In one embodiment, when two points disposed on the flow path and sequentially arranged between the blowing fan and the filter are referred to as a first point and a second point, respectively, the flow rate at the second point may be smaller than the flow rate at the first point. By way of example, the air may have a flow rate of 3 m/s or less while passing through the filter.

In one embodiment, the filter may be a photocatalyst filter and the light source unit may emit UV light.

In one embodiment, the first guide may guide the air such that the flow path of the air has a width gradually increasing from the blowing fan to the filter.

In one embodiment, the filter may be spaced apart from the air outlet.

In one embodiment, the light source unit may be disposed between the blowing fan and the filter.

In one embodiment, the housing may include a ceiling and a bottom surface facing each other and a sidewall connecting the ceiling to the bottom surface, and the light source unit may be provided to at least one of the ceiling, the bottom surface, and the sidewall.

In one embodiment, the first guide may include a first sub-guide and a second sub-guide spaced apart from each other, and a separation distance between the first sub-guide and the second sub-guide may gradually increase from the blowing fan to the filter.

In one embodiment, at least one of the first sub-guide and the second sub-guide may have a curved surface. In one embodiment, at least one of the first sub-guide and the second sub-guide may be convex towards an inner surface of the housing.

In one embodiment, the housing may include a ceiling provided with the air inlet, a bottom surface facing the ceiling, and a sidewall connecting the ceiling to the bottom surface and provided with the air outlet.

In one embodiment, a lower surface of the blowing fan may be tilted with respect to the bottom surface.

In one embodiment, the air purification module may further include a second guide disposed between the bottom surface and the blowing fan and protruding from the bottom surface at an angle corresponding to an inclination of the blowing fan.

In one embodiment, the second guide may be provided as a pair of second guides separated from each other by a distance corresponding to a width of the blowing fan and the second guides may be connected to the first and second sub-guides, respectively.

In one embodiment, the first guide may extend in an upward direction and may have the same height as or a greater height than an installation height of the blowing fan.

In one embodiment, an upper surface of the blowing fan and the first guide may contact the ceiling.

In one embodiment, the blowing fan may have a rotational axis tilted with respect to the bottom surface.

In one embodiment, the air inlet may have the same diameter as or a larger diameter than the blowing fan.

In one embodiment, the air inlet may be formed to overlap the blowing fan.

In one embodiment, the air purification module may further include a light source support supporting the light source unit, and the light source support may be connected to the first guide. The first guide may be integrally formed with the light source support.

Another aspect of the present disclosure relates to a refrigerator including the air purification module. The refrigerator includes: a main body provided with a cooling device and a storage compartment, and the air purification module disposed inside the storage compartment.

Embodiments of the present disclosure provide an air purification module having improved deodorization efficiency.

Embodiments of the present disclosure provide a refrigerator including the air purification module having improved deodorization efficiency.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION OF THE EMBODIMENTS

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, embodiments of the present disclosure will be described in detail with reference to the accompanying drawings.

Figure 1:
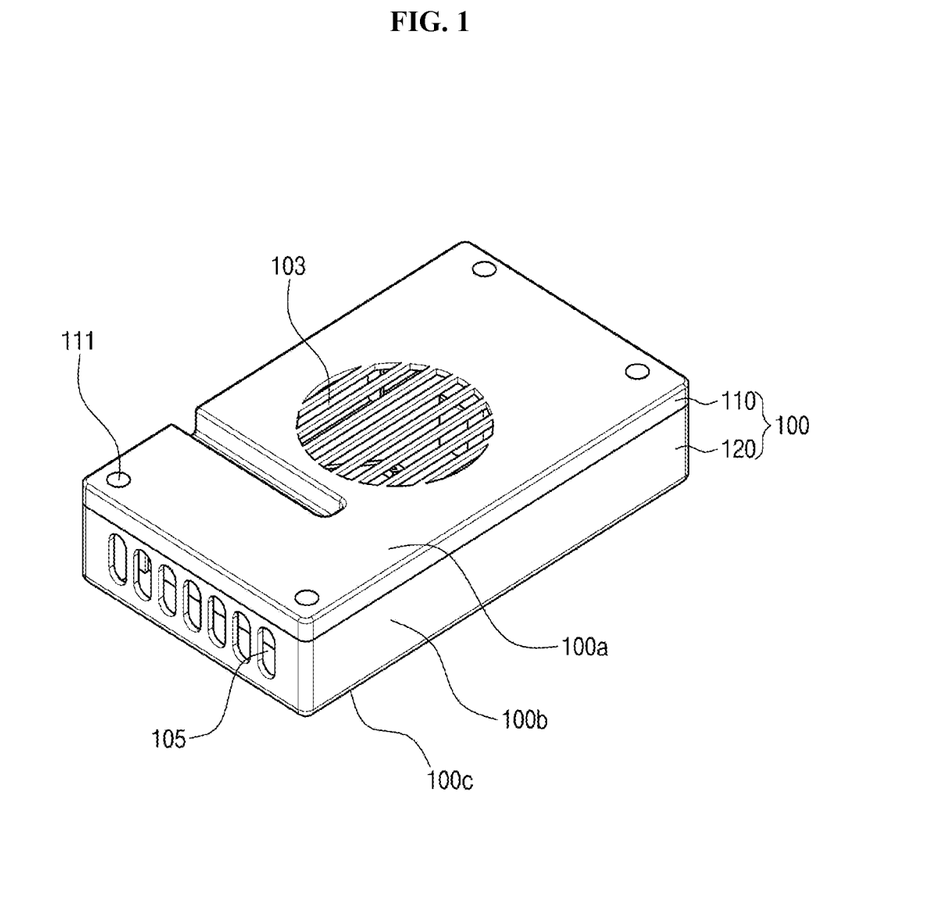
FIG. 1 is a perspective view of an air purification module according to one embodiment of the present disclosure.
Figure 2:
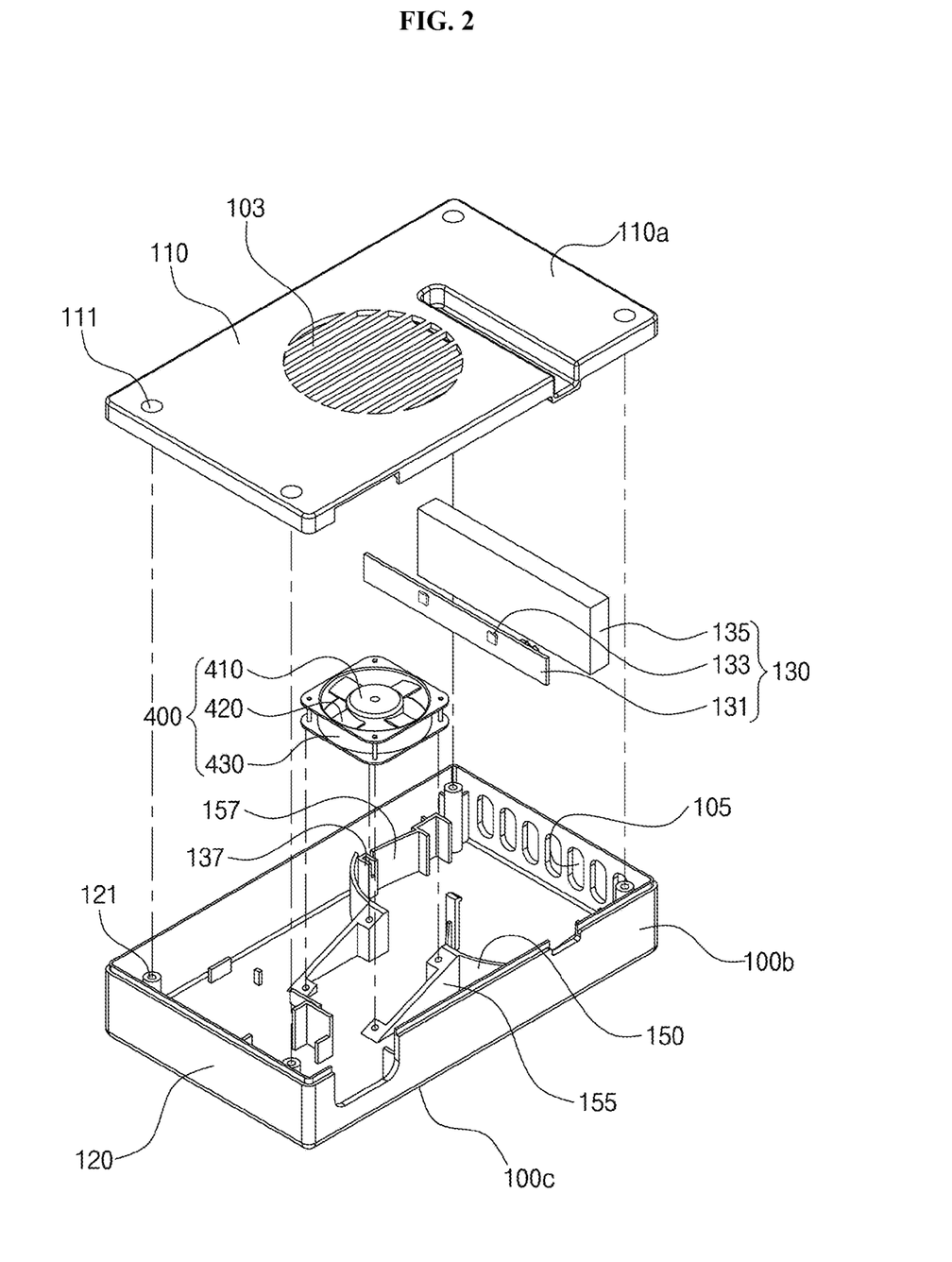
FIG. 2 is an exploded perspective view of the air purification module shown in FIG. 1.
Figure 3A:
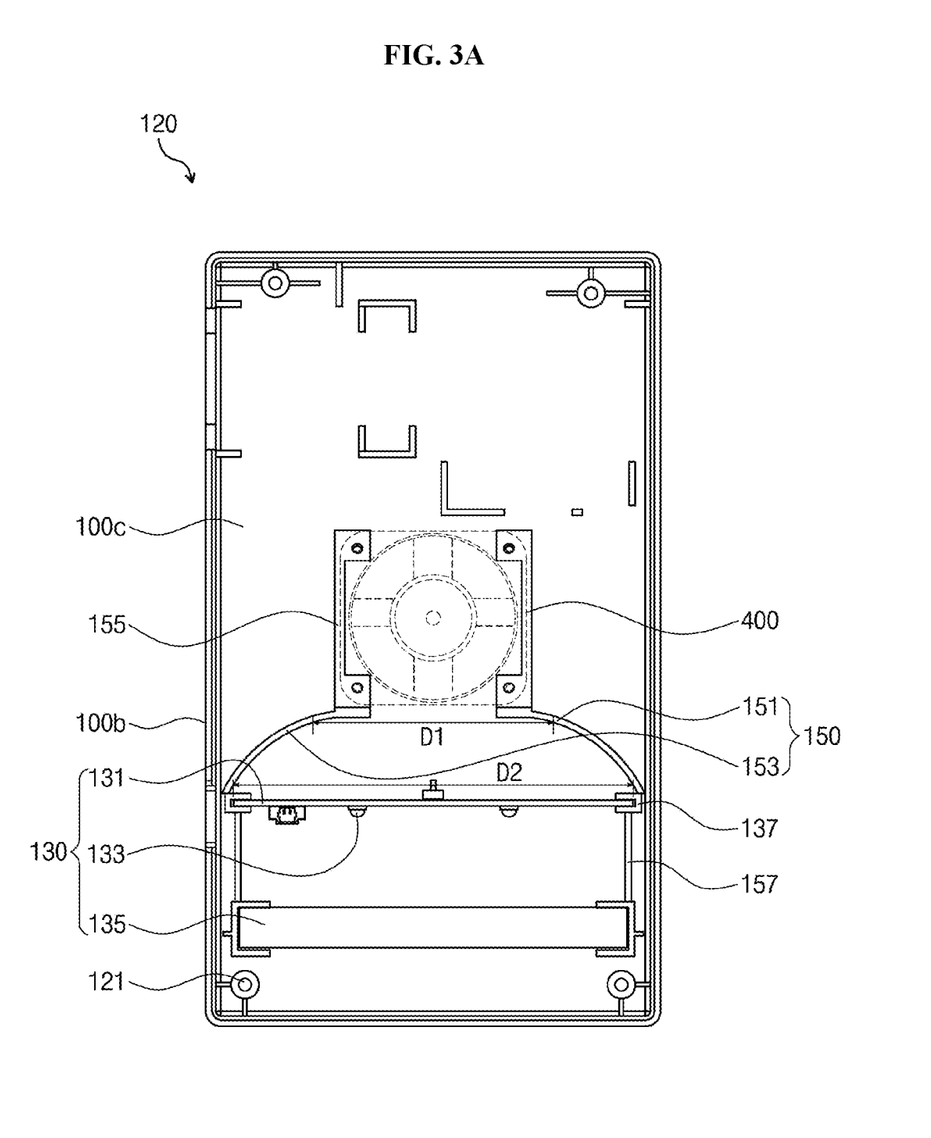
FIG. 3A is a plan view illustrating a relationship between an upper housing and a fan in the air purification module according to the embodiment of the present disclosure.
Figure 3B:
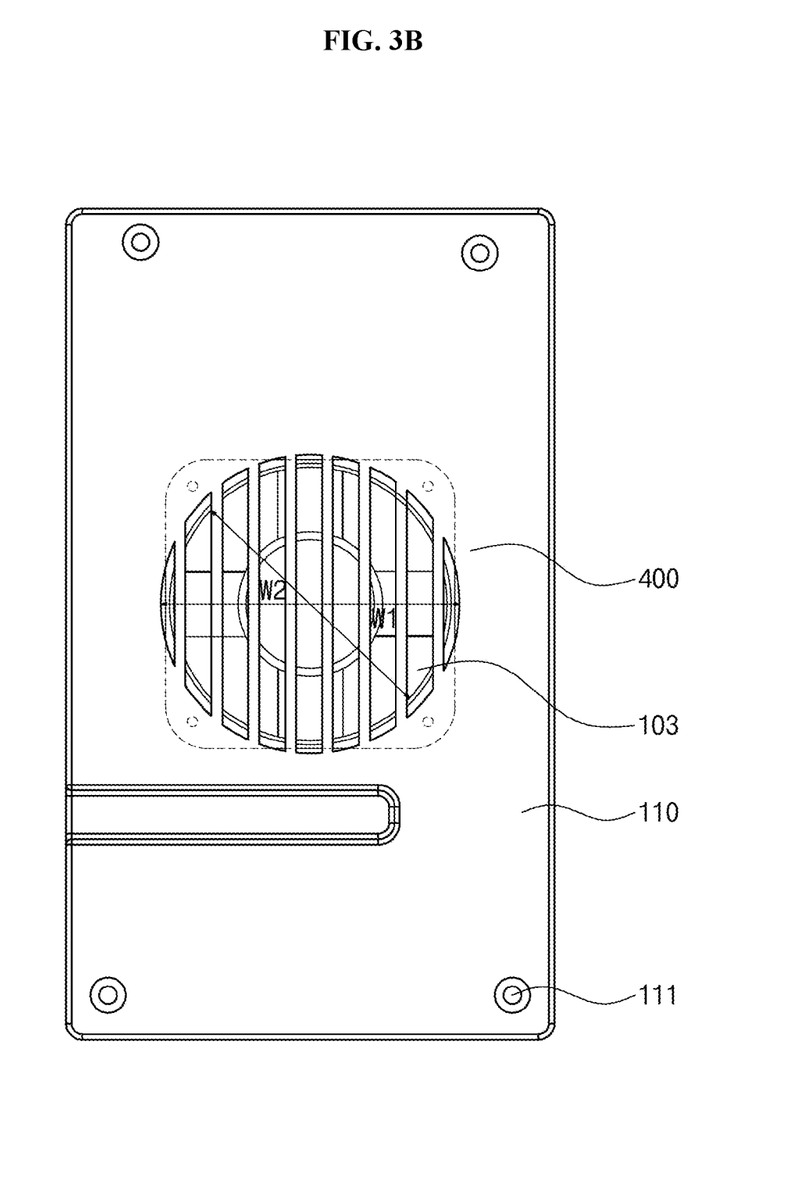
FIG. 3B is a plan view of a lower housing of the air purification module.

FIG. 1 is a perspective view of an air purification module according to one embodiment of the present disclosure and FIG. 2 is an exploded perspective view of the air purification module shown in FIG. 1. FIG. 3A is a plan view illustrating a relationship between an upper housing and a fan in the air purification module according to the embodiment of the present disclosure and FIG. 3B is a plan view of a lower housing thereof.

Referring to FIG. 1, FIG. 2, FIG. 3A and FIG. 3B, the air purification module according to the embodiment of the present disclosure includes a housing 100 having an interior space defined therein, an air purification unit 130 disposed inside the housing 100, a blowing fan 400 suctioning air to supply the air towards the air purification unit 130, and a first guide 150 formed in the interior space of the housing 100 to guide the air to flow from the blowing fan 400 toward a filter 135.

The housing 100 defines an external appearance of the air purification module to provide the interior space in which air is treated. Although the housing 100 defines the external appearance of the air purification module, additional casing or components may be disposed outside the air purification module. In addition, the housing 100 may be provided as a separate component but is not limited thereto. Alternatively, when the air purification module according to the present disclosure is employed in other home appliances or furniture, the housing 100 may be used as an interior component in the other home appliances or furniture. For example, in a refrigerator employing the air purification module according to the present disclosure, an inner wall of the refrigerator or a portion of a storage closet may be used as the housing instead of a separate housing 100.

The housing 100 may include an upper housing 110 and a lower housing 120 coupled to each other to form a rectangular parallelepiped shape defining the interior space therein. In the rectangular parallelepiped shape shown in the drawings, when a surface having an air inlet 103 and facing upwards is referred to as a ceiling 100a, an opposite surface thereto is referred to as a bottom surface 100c, and a portion between the ceiling 100a and the bottom surface 100c is referred to as a sidewall 100b, the upper housing 110 may be constituted by the ceiling 100a and at least part of the sidewall 100b, and the lower housing 120 may be constituted by the bottom surface 100c and at least part of the sidewall 100b. Here, the sidewall 100b may be formed by one of the upper housing 110 and the lower housing 120 or by both the upper housing 110 and the lower housing 120 overlapping each other. Accordingly, the portion referred to as the sidewall 100b means a portion connected to at least one of the upper housing 110 and the lower housing 120.

The upper housing 110 is fastened to the lower housing 120 through a first fastening member 111 and a second fastening member 121 to define the interior space therein. The first fastening member 111 may be provided to the upper housing 110 and the second fastening member 121 may be provided to the lower housing 120. The first and second fastening members 111, 121 may be members for hook coupling, screw coupling, and the like. For example, the first fastening member 111 may be a screw and the second fastening member 121 may be a screw hole into which the screw is inserted. The first and second fastening members 111, 121 are not limited thereto and may be realized in various forms so long as the first and second fastening members can fasten the upper and lower housings 110, 120 to each other.

Although the housing 100 is illustrated as having a substantially rectangular shape, it should be understood that the shape of the housing 100 is not limited thereto and may be modified in various ways without departing from the concept of the present disclosure. The shape of the housing 100 may be modified into various shapes depending upon a mounting region of a home appliance or furniture employing the air purification module. Further, although the ceiling 100a, the bottom surface 100c, and the sidewall 100b are referred to for convenience of description in this embodiment, it should be understood that the ceiling 100a is not limited to an upper side. The ceiling 100a, the bottom surface 100c, and the sidewall 100b may be disposed to face in different directions depending upon a mounting location and direction of the air purification module.

The housing 100 has the interior space provided with the air inlet 103 and the air outlet 105. The air inlet 103 is disposed at one side of the housing 100 and the air outlet 105 is disposed at the other side thereof to be spaced apart from the air inlet 103. The interior space of the housing 100 is formed with a flow path along which air introduced into the interior space through the air inlet 103 flows to the air outlet 105. Each of the air inlet 103 and the air outlet 105 is connected to an outside. External air is introduced into the housing 100 through the air inlet 103 and air inside the housing 100 is discharged from the housing 100 through the air outlet 105. The air flowing through the air inlet 103 and the air outlet 105 is a target that requires treatment, such as sterilization, purification, deodorization, and the like. Here, the exterior may differ depending upon a location or apparatus in which the air purification module is actually placed. For example, when the air purification module is disposed in a storage closet of a home appliance, such as a refrigerator, the exterior may mean a space of the storage closet outside the air purification module. When the air purification module is disposed in a room in a house, the exterior may mean an interior space inside the room.

In embodiments of the present disclosure, the target requiring treatment such as sterilization, purification, deodorization, and the like may change.

In one embodiment, the air inlet 103 is provided to the ceiling 100a and the air outlet 105 is provided to the sidewall 100b, for example, the sidewall 100b of the lower housing 120. Locations of the air inlet 103 and the air outlet 105 may be changed depending upon locations of the light source unit 133, the filter 135, and the blowing fan 400.

The air inlet 103 may be connected to the interior space of the housing 100. The air inlet 103 may be provided in the form of an opening having a substantially circular or elliptical shape in plan view. The air inlet 103 may have a shape corresponding to the blowing fan 400 so as to allow air to be supplied to the blowing fan 400 as easily as possible. Since the blowing fan 400 has a substantially circular shape, the air inlet 103 may also have a circular shape. Here, the air inlet 103 may be provided with a guard frame to protect the blowing fan 400 while blocking an object from approaching the blowing fan 400. The guard frame may be provided in the form of a net or stripe. The guard frame may be integrally formed with the upper housing 110, but it is not limited thereto. Alternatively, the guard frame may be provided as a separate member to be mounted on the upper housing 110 through a fastening member.

In one embodiment, the guard frame of the air inlet 103 is integrally formed with the upper housing 110 and includes bars arranged in a stripe pattern at regular intervals. However, it should be understood that the guard frame of the air inlet 103 is not limited thereto and may be realized in various shapes so long as the guard frame allows air inflow therethrough while preventing an object from damaging the blowing fan 400 and protecting the blowing fan 400.

The interior space of the housing 100 is communicated with the outside through the air outlet 105. The air outlet 105 may have various shapes corresponding to the shape of the sidewall 100b. In this embodiment, the air outlet 105 may be provided in the form of a substantially rectangular-shaped opening. The air outlet 105 may be provided in a shape corresponding to the filter 135 and the sidewall 100b so as to allow air having passed through the filter 135 to be discharged therethrough as easily as possible. Since each of the filter 135 and the sidewall 100b has a substantially rectangular shape, the air inlet 103 may also have a rectangular shape. However, it should be understood that the air outlet 105 is not limited thereto and may have various shapes, for example, a circular shape, an elliptical shape, and the like.

Here, the air outlet 105 may also be provided with a guard frame to protect the filter 135 inside the housing 100 while blocking an object from damaging the housing 100. In one embodiment, the guard frame of the air outlet 105 is integrally formed with the lower housing 120 and includes bars arranged in a stripe pattern at regular intervals. However, it should be understood that the guard frame of the air outlet 105 is not limited thereto and may be realized in various shapes so long as the guard frame allows air flow therethrough while preventing an object from damaging the interior space of the housing 100 and protecting the filter 135.

The blowing fan 400 is disposed inside the interior space of the housing 100 and placed near the air inlet 103. The blowing fan 400 forces air to flow from the air inlet 103 to the air outlet 105. Although various fans may be used as the blowing fan 400, an axial type blowing fan may be used as the blowing fan 400 in this embodiment. For the axial type blowing fan 400, a direction of air flowing towards the fan is substantially the same as a direction of air discharged from the fan.

The axial type blowing fan 400 tends to generate less noise than a centrifugal fan. As compared with the axial type blowing fan 400, the centrifugal fan has problems not only with loud noise, but also with an excessive flow rate in a lateral direction and large force applied to the fan.

The blowing fan 400 includes a rotational shaft 410, which acts as a rotational center, a plurality of blades 420 coupled to the rotational shaft 410 to rotate, and a holding frame 430 that holds and supports the rotational shaft 410 to allow the rotational shaft 410 and the blades 420 to be stably rotated.

In this embodiment, the blowing fan 400 is tilted with respect to the bottom surface 100c. In other words, an upper surface of the blowing fan 400 is tilted with respect to the ceiling 100a of the housing 100 and a lower surface of the blowing fan 400 is tilted with respect to the bottom surface 100c of the housing 100. Since the rotational shaft 410 of the blowing fan 400 is disposed in a normal direction with respect to the lower surface of the blowing fan 400, the rotational shaft 410 of the blowing fan 400 is also tilted with respect to the bottom surface 100c.

In some embodiments, no structure obstructing the air flow is disposed between the ceiling 100a of the housing 100 and the blowing fan 400. Accordingly, air can be easily supplied from the air inlet 103 on the ceiling 100a of the housing 100 to the blowing fan 400. In other embodiments, an air guide structure may be provided to guide air flow as needed.

A second guide 155 is disposed between the bottom surface 100c of the housing 100 and the blowing fan 400 and protrudes from the bottom surface 100c at an angle corresponding to an inclination of the blowing fan 400 such that the blowing fan 400 is tilted with respect to the bottom surface 100c. The second guide 155 may have a wedge shape, as shown in FIG. 2. For example, the second guide 155 may have a right-angled triangle shape in side view, in which the blowing fan 400 is disposed on a plane corresponding to an oblique side of the right-angled triangle, as shown in FIG. 2. The shape of the second guide 155 is not limited thereto and may have a different shape.

The second guide 155 may include as a pair of second guides separated from each other by a predetermined width to support the blowing fan 400 at both sides thereof. Further, in plan view, the second guides 155 may have a shape extending only towards the filter 135 to allow air discharged from the blowing fan 400 to flow only towards the filter 135. In this embodiment, a separation distance between the pair of second guides 155 may correspond to the width of the blowing fan 400, whereby the air discharged from the blowing fan 400 flows along a space between the pair of second guides 155. The second guides 155 is structured and positioned to provide a flow path below the blowing fan 400. The second guides 155 can prevent the air from flowing in directions other than a direction towards the filter 135 described below.

In one embodiment, a separate guide may be further disposed above the blowing fan 400 like the second guide 155 disposed below the blowing fan 400. For example, although not shown in the drawings, a separate wedge type guide may be further disposed between the ceiling 100a of the housing 100 and the blowing fan 400 to allow the air having passed through the air inlet 103 to flow only towards the blowing fan 400.

In one embodiment, the blowing fan 400 may be disposed at a location corresponding to the air inlet 103 of the housing 100. In other words, the blowing fan 400 may be disposed to overlap the air inlet 103 of the housing 100 in plan view. Here, the air inlet 103 may have the same diameter as or a larger diameter than that of the blowing fan 400. For example, when the diameter of the air inlet 103 is referred to as a first diameter W1 and the diameter of the blowing fan 400 is referred to as a second diameter W2, the first diameter W1 may be larger than or equal to the second diameter W2. According to this embodiment, the air inlet 103 is formed to have the same diameter as or a larger diameter than the blowing fan 400, thereby allowing easy supply of air to the blowing fan 400. Here, the diameter of the blowing fan 400 means a diameter of a region thereof, through which air is discharged from the blowing fan 400 upon rotation of the blades 420, and may be an inner diameter of a support frame which supports the rotational shaft 410 and the blades 420 to be disposed therein.

Referring again to FIG. 1 and FIG. 2, the air purification unit 130 adapted to purify air is disposed on the flow path of the air. The air purification unit 130 is disposed between the blowing fan 400 and the air outlet 105 in the flow path. The air purification unit 130 includes the filter 135 and a light source unit emitting light towards the filter 135. The light source unit is disposed inside the housing 100 and emits light. The light source unit may include a substrate 131 and at least one light emitting device 133 mounted on the substrate 131 and emitting light, as shown in FIG. 2.

The light source unit may be disposed on at least one of the ceiling 100a, the bottom surface 100c, and the sidewall 100b of the housing 100. In one embodiment, the light source unit is disposed on the bottom surface 100c.

The light source unit is spaced apart from the filter 135 and emits light towards the filter 135. In this embodiment, the light source unit may be directly disposed on an upper surface of the bottom surface 100c to contact the upper surface thereof, without being limited thereto. Alternatively, the light source unit may not contact the bottom surface 100c so long as the light source is spaced apart from the filter 135 so as to supply light to the filter 135. For example, the light source unit may be connected to a separate light source support 137 protruding from the bottom surface 100c, the sidewall 100b, or the ceiling 100a.

Light emitted from the light source unit may have various wavelength bands. The light emitted from the light source unit may be light in the visible spectrum, in the UV wavelength band, or in other wavelength bands.

In one embodiment, the wavelength band of light emitted from the light source unit may differ depending upon the kind of filter 135 described below.

In some embodiments, the light source unit may be provided in the form of a sheet light source and/or a spot light source. In another embodiment, the light source unit may be provided in the form of a spot light source. In FIG. 2, the light source unit is provided in the form of the spot light source.

The substrate 131 may be provided in a plate shape. The substrate 131 may be elongated in a predetermined direction or may be provided in various shapes capable of mounting the light emitting device 133, such as a circular shape, an elliptical shape, a polygonal shape, and the like.

The substrate 131 may be provided on at least one surface thereof with at least one, for example, multiple light emitting devices 133. When the light emitting device 133 is provided in plural, the light emitting devices 133 may be disposed randomly, in a particular arrangement, in a linear arrangement, or in various arrangements including a zigzag arrangement. Here, the light emitting devices 133 may be disposed such that the maximum area of the filter 135 can be irradiated with light emitted therefrom as uniformly as possible.

For the light source unit including the multiple light emitting devices 133, each of the light emitting devices 133 may emit light in the same wavelength band or in different wavelength bands. For example, in some embodiments, all of the light emitting devices 133 may emit light in the UV wavelength band. In other embodiments, some light emitting devices 133 may emit light in some fraction of the UV wavelength band and the other light emitting devices 133 may emit light in the other fraction of the UV wavelength band. By way of example, some light emitting devices 133 may emit light in the wavelength band of about 320 nm to about 400 nm and the other light emitting devices 133 may emit light in a different wavelength band. When the light emitting devices 133 emit light in different wavelength bands, the light emitting devices 133 may be arranged in various shapes and sequences.

However, it should be understood that the wavelength band of light emitted from the light emitting devices 133 is not limited to the aforementioned range. In other embodiments, the light emitting devices 133 may emit not only UV light but also light in the visible spectrum.

In one embodiment, the light source unit may emit light towards the filter 135. As shown in FIG. 2, in the structure where the light emitting devices 133 are disposed on one surface of the substrate 131, the light source unit may emit light in a direction perpendicular to the surface of the substrate 131 on which the light emitting devices 133 are disposed. However, the direction of light emitted from the light source unit may be changed in various ways.

In one embodiment, the housing 100 may be provided with a light source support 137 that secures and supports the light source unit. The light source support 137 may be provided to at least one of the ceiling 100a, the sidewall 100b, and the bottom surface 100c of the housing 100.

The filter 135 is disposed in the interior space of the housing 100. The filter 135 is placed adjacent the air outlet 105 while being spaced apart from the air outlet 105. When the filter 135 is placed too near the air outlet 105, the air flow can be obstructed by the guard frame of the air outlet 105, thereby obstructing a purification function of the filter 135.

The filter 135 serves to purify air and may be selected from among various kinds of filters. In one embodiment, the filter 135 may be a photocatalytic filter 135.

In one embodiment, the filter 135 may have a rectangular parallelepiped shape having relatively broad front and back surfaces. The filter 135 may be elongated in one direction and may have a size corresponding to the size of the air outlet 105 of the housing 100. The air outlet 105 is covered by the filter 135.

In one embodiment, the filter 135 may have the same diameter as or a larger diameter than that of the blowing fan 400 in the longitudinal direction thereof. In one embodiment, the filter 135 may have a larger diameter than the blowing fan 400 in the longitudinal direction thereof. As the filter 135 has a larger diameter than the blowing fan 400 in the longitudinal direction thereof, the flow rate of air reaching the filter 135 is much slower than the flow rate of the air reaching the blowing fan 400, thereby increasing the air purification effect by increasing a time for which air is exposed to the surface of the filter 135.

The filter 135 may be provided with protrusions or through-holes to increase an air contact area. According to this embodiment, the filter 135 has a plurality of through-holes formed through the front and back surfaces of the filter 135 such that air can flow through the through-holes.

The bottom surface 100c, the sidewall 100b and/or the ceiling 100a of the housing 100 may be provided with a filter securing portion to mount the filter 135 in the interior space of the housing 100. For example, the sidewall 100b of the lower housing 120 may be provided with an insertion groove or a protrusion by which the filter 135 can be slidably coupled to the housing 100. With this structure, the filter 135 may be separately manufactured to be inserted into or drawn from the housing 100 and may be easily replaced by a new filter, as needed.

The filter 135 is spaced apart from the light source unit and is disposed to face an air flow direction. The filter 135 is tilted with respect to the blowing fan 400 while facing the blowing fan 400, whereby the air discharged from the blowing fan 400 is discharged from the housing through the air outlet 105 after passing through the filter 135.

In one embodiment, when the filter 135 is the photocatalytic filter, the filter 135 includes a photocatalyst to treat air through reaction with light emitted from the light source unit. The photocatalyst is a material causing catalytic reaction upon irradiation with light.

The photocatalyst can react with light in various wavelength bands depending upon a substance constituting the photocatalyst. In one embodiment, a substance causing photocatalytic reaction in the UV wavelength band may be used. However, the kind of photocatalyst is not limited thereto and in other embodiments, other photocatalysts having the same or similar mechanism may be used depending upon various wavelengths of light emitted from the light emitting devices 133.

The light source unit emits light in a wavelength band suitable for a reaction wavelength band of the photocatalyst. That is, the light source unit may emit light in some fractions of a wavelength band or light in various wavelength bands depending upon the substance of the photocatalyst. For example, the light source unit may emit light in the UV wavelength band. In this case, the light source unit may emit light in the UV wavelength band of about 100 nm to about 420 nm. In another embodiment, the light source unit may emit light in the UV wavelength band of about 250 nm to about 285 nm and/or in the UV wavelength band of about 300 nm to about 420 nm. The light emitting devices 133 may be selected from among any type of light emitting devices emitting light in a wavelength band allowing reaction with the photocatalyst substance without limitation. For example, for the light source unit emitting light in the UV wavelength band, various kinds of light emitting diodes adapted to emit UV light may be used. For the light source unit emitting light in the visible spectrum, various kinds of light emitting diodes adapted to emit visible light may be used.

The photocatalyst is activated by UV light to decompose various contaminants, bacteria in the air through redox reaction.

The photocatalyst causes chemical reaction generating holes and electrons when exposed to light having intensity greater than or equal to band-gap energy. As a result, compounds in air, for example, water or organic materials, may be decomposed by hydroxyl radicals and superoxide ions generated by photocatalytic reaction. The hydroxyl radicals are substances having very strong oxidation power and provide a deodorization effect by decomposing organic contaminants in air and organic contaminants adsorbed to the filter 135. Further, the hydroxyl radicals remove contaminants, such as bacteria, by deactivating the contaminants in the air.

Such a photocatalyst substance may include titanium oxide ($TiO_2$), zinc oxide (ZnO), tin oxide ($SnO_2$), and the like. In one embodiment, since the recombination rate of electrons and holes generated on the surface of the photocatalyst is very high, there is a limit in use of the photocatalyst for photochemical reaction. Thus, metals, such as Pt, Ni, Mn, Ag, W, Cr, Mo, Zn, and the like, and oxides thereof may be added thereto in order to reduce the recombination rate of electrons and holes. If the recombination rate of holes and electrons is reduced, the possibility of contact with a target material to be oxidized and/or decomposed increases, thereby increasing reactivity of the photocatalyst substance. In addition, an oxide may be added to the photocatalyst substance to improve performance thereof through adjustment of a photocatalyst band gap. Air can be sterilized, purified, and deodorized through such photocatalyst reaction described above. In particular, for sterilization, the photocatalyst can promote sterilization or antibacterial reaction by destroying enzymes in cells of bacteria and enzymes acting on the respiratory system, thereby preventing propagation of bacteria or fungi while decomposing toxins released therefrom.

In particular, according to one embodiment, the photocatalyst may include titanium oxide ($TiO_2$). Upon irradiation with UV light having a wavelength of 400 nm or less, titanium oxide generates hydroxyl radicals and superoxide ions, which decompose organic substances into water and carbon dioxide through redox reaction. Titanium dioxide may be provided in the form of nanoparticles to generate a large amount of hydroxyl radicals even when the light emitting devices 133 emit light having a relatively weak ultraviolet wavelength. Therefore, the photocatalyst has excellent decomposition capability in decomposition of organic materials, exhibits continuous durability and stability despite environmental change, and can be semi-permanently used. Furthermore, hydroxyl radicals generated in large quantities can remove not only organic materials, but also various substances, such as odor-causing substances and bacteria.

In this embodiment, since the photocatalyst acts as a catalyst and does not change by itself, the photocatalyst can be used semi-permanently and can ensure that the effects of the photocatalyst semi-permanently continue so long as light in a corresponding wavelength band is provided thereto.

As shown in FIGS. 2 and 3A, the first guide 150 is disposed between the blowing fan 400 and the filter 135. The first guide 150 guides a flow direction of air such that air flowing from the blowing fan 400 to the filter 135 efficiently flows towards the air purification unit 130 as much as possible.

The first guide 150 is provided in the form of an elongated sheet extending from the blowing fan 400 towards the air purification unit 130 (for example, towards the light source unit). In this embodiment, the first guide 150 may include first and second sub-guides 151, 153 spaced apart from each other, in which both the first and second sub-guides 151, 153 may be provided in the form of elongated sheets, as shown in FIG. 3A. In the extending direction of the first and second sub-guides 151, 153, one end of each of the first and second sub-guides 151, 153 is connected to or disposed near the second guide 155 disposed under one side of the blowing fan 400 and the other end thereof is connected to or disposed near a distal end of one side of the light source unit. The length of each of the first and second sub-guides 151, 153 may be adjusted so as to allow control of directionality of the first and second sub-guides 151, 153. Here, a transverse direction of the first and second sub-guides 151, 153 may be substantially perpendicular to a plane constituting the bottom surface 100c. The first and second sub-guides 151, 153 may be placed at the same height or higher than an installation height of the fan from the bottom surface 100c in order to prevent air supplied from the fan from flowing in directions other than the direction of the filter 135.

The longitudinally extending direction of the first and second sub-guides 151, 153 corresponds to a direction from the pair of second guides 155 to the air purification unit 130 (particularly, to the light source unit). As shown in FIG. 3A, in plan view, the first sub-guide 151 may extend from one side of one of the second guides 155 towards the distal end of one side of the light source unit and the second sub-guide 153 may extend from one side of the other second guide 155 to a distal end of the other side of the light source unit. In one embodiment, the pair of second guides 155 may be connected to the first and second sub-guides 151, 153, respectively, and may be integrally formed therewith.

In this embodiment, the first guide 150 guides the air flow such that the flow path of the air gradually increases from the blowing fan 400 towards the filter 135. In other words, the width between the first and second sub-guides 151, 153, that is, a separation distance between the first and second sub-guides 151, 153, gradually increases from the blowing fan 400 towards the filter 135. Further, at least one of the first sub-guide 151 and the second sub-guide 153 may have a curved surface and may be convex in a direction deviating from the flow path, that is, in a direction towards the inner surface of the housing 100.

In this structure, the air flow rate gradually decreases from the blowing fan 400 towards the filter 135. When two points disposed on the flow path and sequentially arranged between the blowing fan 400 and the filter 135 are referred to as a first point and a second point, respectively, a second width D2 in a perpendicular direction to the flow path at the second point may be greater than a first width D1 in a perpendicular direction with respect to the flow path at the first point. The flow rate at the second point is decreased below the flow rate at the first point corresponding to increase in width. As a result, the first guide 150 serves to guide the direction of the flow path while reducing the flow rate of the air flowing from the blowing fan 400 towards the filter 135. In this embodiment, the first guide 150 is illustrated as having the shape extending from one side of the blowing fan 400 or from the end of the second guide 155 to the light source unit of the air purification unit 130. A third guide 157 is further formed from the light source unit to the filter 135. The third guide 157 is provided in the form of substantially maintaining the width (i.e., D2 in FIG. 3A) increased by the first guide 150 and the flow rate of air at the end of the first guide 150 is substantially the same as the flow rate of air reaching the filter 135.

According to one embodiment of the invention, a period of time for which air contacts the filter 135 is increased by reducing the flow rate of air reaching the filter 135, thereby improving deodorization efficiency. In one embodiment, the flow rate of air reaching the filter 135 may be kept to about 3 m/s or less by increasing the separation distance between the first and second sub-guides 151, 153 of the first guide 150. In another embodiment, the flow rate of air reaching the filter 135 may be kept to about 2.5 m/s or less. With this range of the flow rate, the air purification module can improve deodorization efficiency without significantly reducing a deodorized quantity of air per unit time.

In the above embodiment, the first guide 150 extends from one side of the blowing fan 400 or one end of the second guide 155 to the light source unit of the air purification unit 130 and an additional guide is disposed from the light source unit to the filter 135. The additional guide is provided in the form of substantially maintaining the width increased by the first guide 150, whereby the flow rate of air at the end of the first guide 150 is substantially the same as the flow rate of air reaching the filter 135.

In one embodiment, the flow rate of air described above may be easily achieved using the axial type blowing fan 400. The axial type blowing fan 400 generates not only less noise than an existing centrifugal fan, but also provides a suitable flow rate for deodorization. As compared with the axial type blowing fan, the existing centrifugal fan not only generate severe noise, but also an excessive flow rate in the lateral direction and large force applied to the fan. Accordingly, the existing centrifugal fan does not allow air to remain on the filter 135 for a sufficient period of time due to high flow rate thereof, thereby causing deterioration in deodorization efficiency. According to the embodiment of the present disclosure, the air purification module may purify air in a certain closed external space (for example, a storage compartment of a refrigerator) while circulating the air through the air purification module. In this case, purification operation including sufficient deodorization is more important than providing a rapid flow rate.

Air flows along the flow path from the lower surface of the blowing fan 400 to the surface of the filter 135. When the air reaches a location near the blowing fan 400, the second guide 155 guides the air, which in turn is guided by the first guide 150. Both the first and second guides 150, 155 prevent the air from flowing in the lateral direction or in an opposite direction other than the direction from the blowing fan 400 to the filter 135. Without having first and second guides 150, 155, a surrounding region of the blowing fan 400 is generally open without any structure and an eddy of air discharged from the blowing fan 400 may generate, along with an unstable air stream, excessive decrease in a flow rate only in some regions, and the like. As a result, all of the air discharged from the blowing fan 400 cannot reach the filter 135. Moreover, the flow rate of the air reaching the filter 135 becomes unstable, thereby deteriorating air purification efficiency. Conversely, in the embodiments of the present disclosure, the first and second guides 150, 155 are disposed between the blowing fan 400 and the filter 135, thereby preventing non-uniformity and excessive reduction in the flow rate.

In some embodiments, the filter 135 may have a larger area than the blowing fan 400 such that the separation distance between the first and second sub-guides 151, 153 of the first guide 150 is gradually increased from the blowing fan 400 to the filter 135 corresponding to the size of the filter 135, thereby allowing the air to uniformly contact the overall area of the filter 135. Further, in this structure, the area of the flow path is gradually increased from the blowing fan 400 to the filter 135, whereby the flow rate of the air is gradually decreased from the blowing fan 400 towards the filter 135. As the flow rate of the air is decreased, the air can react with the filter 135 for a sufficient period of time.

Although the lower housing 120 is provided with the first guide 150 in this embodiment, it should be understood that other implementations are possible. The first guide 150 may be provided to at least one of the upper housing 110 and the lower housing 120. Further, the first guide 150 may be integrally formed with the upper housing 110 and/or the lower housing 120.

In the air purification module with the above structure, the first and/or second guides 150, 155 are disposed in the space between the blowing fan 400 and the filter 135 to prevent the flow rate of the air supplied to the filter 135 from becoming unstable or from being reduced, thereby improving an air treatment effect, for example, a deodorization effect.

The air purification module according to the embodiments of the present disclosure may be modified in various ways within the concept of the present disclosure. By way of example, the air purification module according to the embodiments of the present disclosure may have various shapes of guides.

Figure 4:
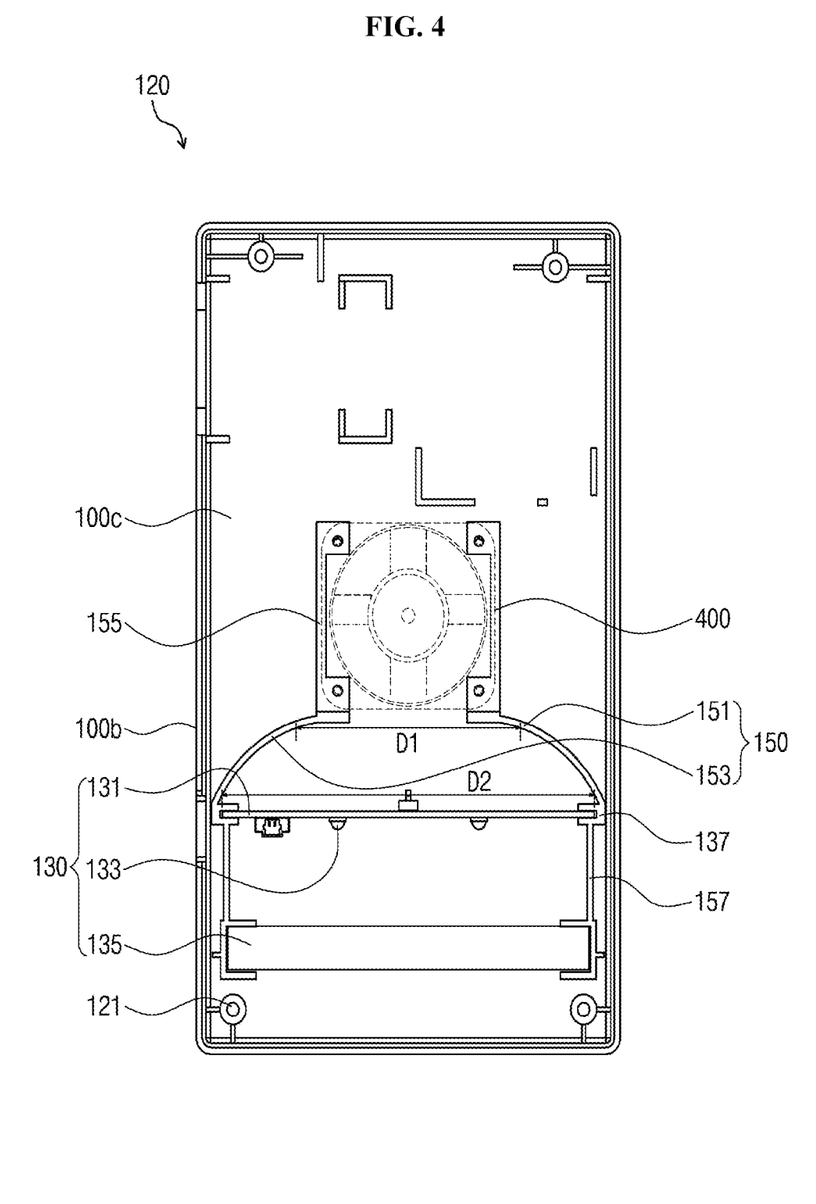
FIG. 4 is a plan view illustrating a part of the air purification module according to the embodiment of the present disclosure.

FIG. 4 is a plan view illustrating a part of an air purification module according to one embodiment of the present disclosure. The following description will focus on different features than the above embodiments, and, for parts of the air purification module not described below, refer to the description of the above embodiments.

At least two selected from among the first to third guides 150, 155, 157 and the light source supports 137 may be formed with each other. Referring to FIG. 4, the first guide 150, the third guide 157, and the light source supports 137 are formed with one another. By way of example, the first guide 150, the third guide 157, and the light source supports 137 may be integrally formed with one another so as not to be separated from one another. In particular, the light source supports 137 are disposed at end of the first guide 150 and, with the third guide 157 disposed between the light source supports 137, the first guide 150, the light source supports 137, and the third guide 157 are connected to one another, thereby improving rigidity of a support structure of each of components inside the housing 100.

In addition, the air purification module according to the embodiment of the invention may include a modified first guide 150 to allow air to flow from the blowing fan 400 to the filter 135 as efficiently as possible.

Figure 5:
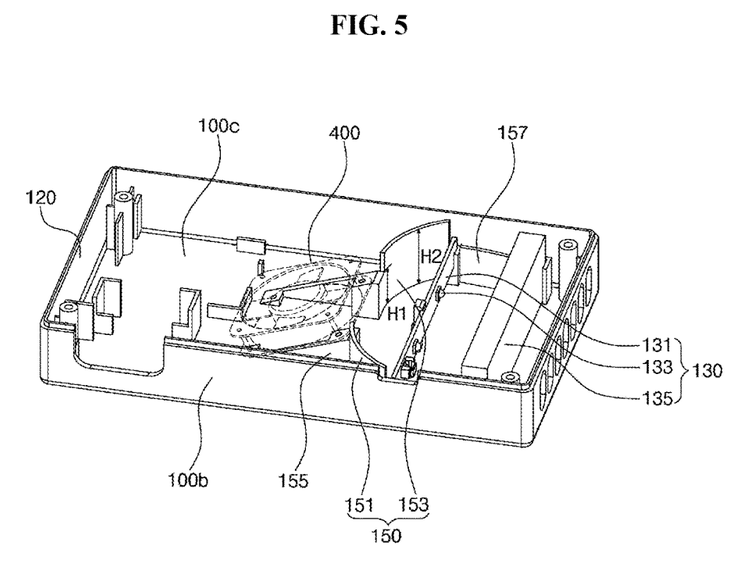
FIG. 5 is a perspective view of a part of the air purification module according to the embodiment of the present disclosure.

FIG. 5 is a perspective view of a part of the air purification module according to the embodiment of the present disclosure.

Referring to FIG. 5, the first and second sub-guides 151, 153 may protrude from the bottom surface 100c such that upper portions thereof contact the ceiling in order to prevent air introduced into the housing by the blowing fan from flowing in a direction other than a direction of the filter 135.

In particular, the first and second sub-guides 151, 153 may extend upwards to a predetermined height, for example, a height of the blowing fan 400, in a region in which the blowing fan 400 is not disposed. Accordingly, when the height of the first guide 150 is referred to as a first height H1 in a region in which the blowing fan 400 is disposed and the height of the first guide is referred to as a second height H2 in the region in which the blowing fan 400 is not disposed, the second height H2 corresponds to a value obtained by adding the height of the blowing fan 400 to the first height H1.

Further, the second height H2 may be substantially the same as a distance from the bottom surface 100c of the housing 100 to the ceiling 100a of the housing 100. In this embodiment, the upper surface of the blowing fan 400 and the upper portion of the first guide 150 may contact the ceiling 100a of the housing 100. Accordingly, all of the air introduced into the housing by the blowing fan 400 flows towards the air purification unit 130 without flowing to other regions inside the housing 100.

As a result, according to this embodiment, the air purification module can purify larger quantities of air by increasing the quantity of air flowing towards the filter 135, despite reduction in flow rate of the air as compared with the above embodiments.

In the above embodiments, the air purification module includes one blowing fan 400 and one air purification unit. However, it should be understood that other implementations are possible in various ways within the concept of the present disclosure. For example, in some embodiments, the blowing fan 400 and/or the air purification unit may be provided in plural. The air purification module may include two or more blowing fans 400 depending upon the quantities of air to be treated by the air purification module, or the area or shape of the installation region of the air purification module.

The air purification module according to some embodiments of the present disclosure described above may include a light source unit and a filter having various shapes, in which the light source unit may be disposed in various directions and the number of light source units may be set in various ways.

For example, the light source unit and the filter may be disposed at an angle or parallel to the flow direction of air. Here, the substrate of the light source unit may be spaced apart from the filter to be substantially parallel to the filter. In the above embodiment, the filter is disposed to face the flow direction of the air and thus the flow path is formed to penetrate the filter. Alternatively, the flow path may be parallel to the filter and the light source unit. In other words, although there can be a slight inclination with respect to the front or back surface of the filter, the air may be forced to flow generally in a direction parallel to the front or back surface of the filter instead of penetrating the filter. In this case, the front or back surface of the filter may be parallel to the flow direction of the air, that is, the flow path of the air.

In one embodiment, a sensor may be disposed in a region other than the flow path to detect various substances in air. The sensor may detect whether dust, certain gas, organic materials, and the like are present in the air, and, if any, the kind of matter in the air or the amount of the matter.

Data relating to the kind and amount of a target substance detected by the sensor may be associated with operation of the air purification module, and the air purification module according to some embodiments may further include a drive unit (not shown) that receives the data from the sensor and controls the blowing fan 400 and/or the light source unit. The detection data include the presence/absence of target substances, the kinds and/or amounts of target substances, and the like.

With the structures described above, the air purification module according to the embodiments of the present disclosure may be applied to various home appliances or furniture.

Figure 6:
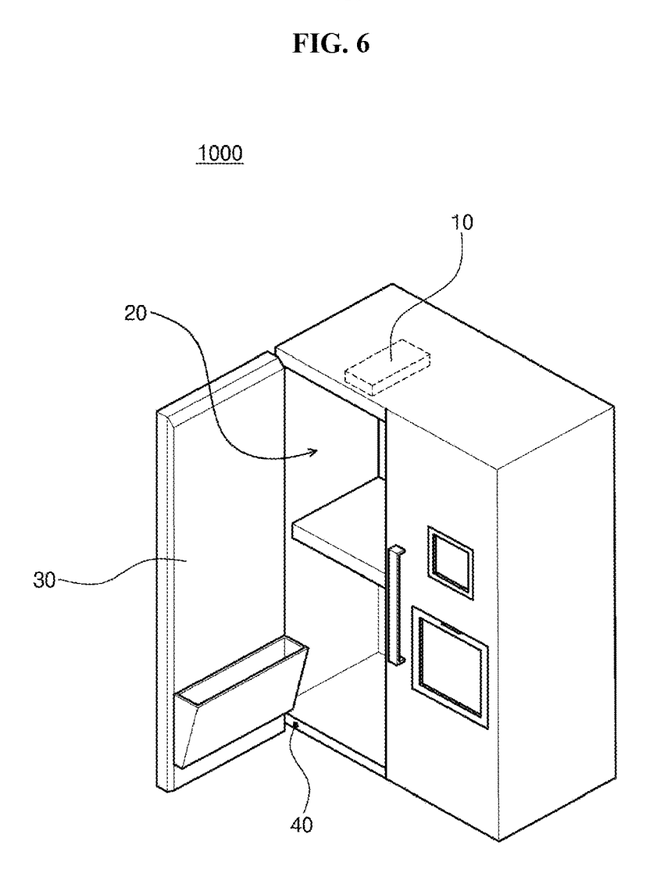
FIG. 6 is a view of a refrigerator including an air purification module according to one embodiment of the present disclosure.

FIG. 6 is a view of a refrigerator including an air purification module according to one embodiment of the present disclosure. However, it should be understood that the air purification module according to the embodiments of the present disclosure may be applied not only to the refrigerator but also to other home appliances, furniture, and constructions, which require treatment of air, such as deodorization, purification, and the like.

A refrigerator 1000 according to one embodiment of the present disclosure may include a main body 20, which is provided with a cooler and having a storage compartment defined therein, and an air purification module 10 according to one or more of the above embodiments of the present disclosure disposed in the storage compartment.

The main body 20 has at least one storage compartment and the air purification module may be disposed in a suitable region in the storage compartment. The main body 20 is provided with at least one door 30 which opens or closes the storage compartment, and a sensor 40 disposed at one side of the main body 20 to face the door 30 and detecting whether the door is open or closed. In some embodiments, the sensor 40 may be provided in the form of a switch that is pressed when the door is closed.

In the refrigerator 1000 according to this embodiment, when the door 30 is closed, the air purification module 10 may be turned on. When the air purification module 10 is turned on, air in the storage compartment is purified. If the door 30 is open, the air purification module 10 may be turned off.

The air purification module according to the embodiments of the invention has an excellent deodorization effect. Some experiments were carried out using the air purification module according to the embodiments of the present disclosure and the following results were obtained.

Figure 7:
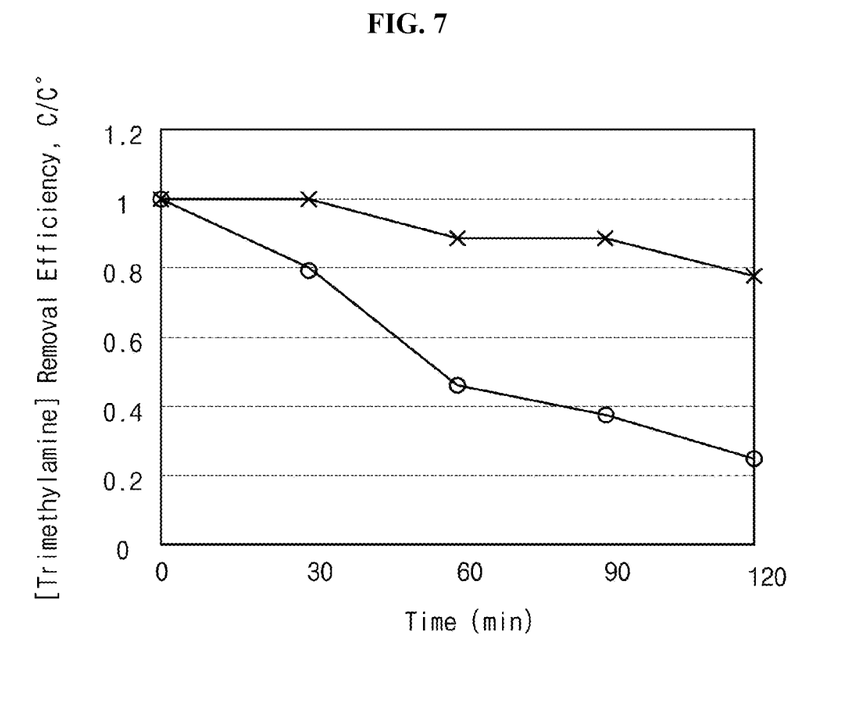
FIG. 7 is a graph depicting a deodorization effect in a storage compartment of a refrigerator including the air purification module according to the embodiment of the present disclosure.

FIG. 7 is a graph depicting a deodorization effect in the storage compartment of the refrigerator including the air purification module according to the embodiment of the present disclosure. In this graph, a curve marked by "x" symbols shows time-dependent concentration changes of Trimethylamine (hereinafter, "TMA") in a storage compartment of a refrigerator not including an air purification module and a curve marked by "o" symbols shows time-dependent concentration changes of TMA in the storage compartment of the refrigerator including the air purification module according to the embodiment of the present disclosure. In this graph, the y axis indicates the ratio of a TMS concentration after a certain period of time to an initial TMA concentration. In this experiment, the storage compartment of the refrigerator had a volume of 400 L and was kept at 4° C. As a contaminant for confirmation of deodorization, TMA (trimethylamine) was used and an initial concentration of TMA was 5±1 ppm. As a filter in the air purification module, a photocatalyst filter having a size of 75 mm×25 mm×8 m was used. As a light source of the air purification module, two LEDs emitting UV light having a wavelength of 365 nm were used and separated from the filter by a distance of 20 mm, and had IF of 300 mA and an average radiance of 19.02 mW/cm². The blowing fan was a DFM 3510B and operated at 12 V.

Table 1 shows removal efficiency of TMA in the refrigerator including the air purification module according to the embodiment of the invention under conditions of FIG. 7.

TABLE 1

| Time (min) | TMA removal efficiency (%) |
| --- | --- |
| 0 | — |
| 30 | 20.8 |
| 60 | 54.2 |
| 90 | 62.5 |
| 120 | 75.0 |

Referring to FIG. 7 and Table 1, it could be seen that the refrigerator including the air purification module according to the embodiment of the invention exhibited significant reduction in concentration of a substance having an unpleasant smell, that is, TMA, over time. In particular, it could be seen that the concentration of TMA was reduced to about a quarter of the initial concentration thereof about 2 hours after operation of the air purification module. Here, it could be seen that the refrigerator not including the air purification module exhibited slight reduction in concentration of TMA and it seems that this result was obtained due to adsorption of TMA to an inner wall of the storage compartment of the refrigerator. As described above, it could be seen that the refrigerator including the air purification module according to the embodiment of the present disclosure had a very good deodorization effect with respect to the substance having an unpleasant smell over time.

Figure 8:
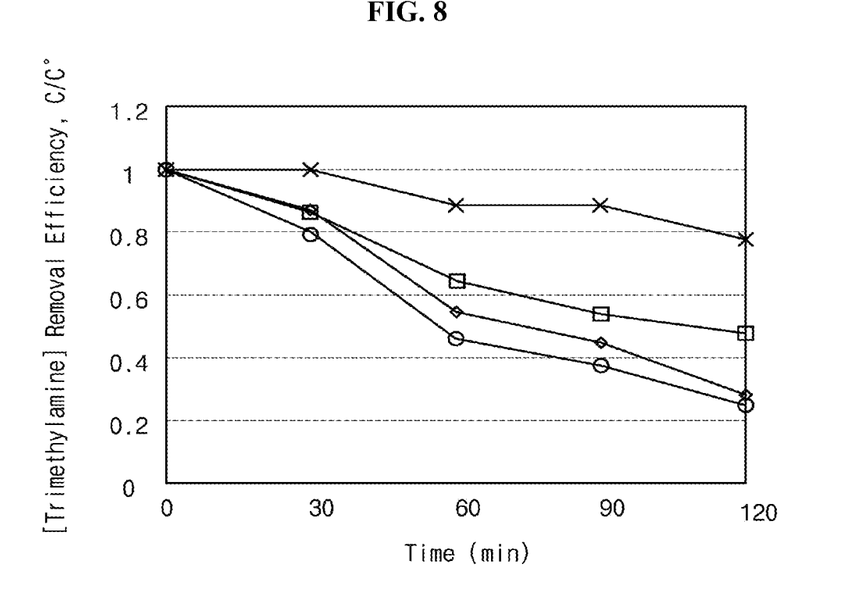
FIG. 8 is a graph comparing a deodorization effect in a storage compartment of a refrigerator including an air purification module of one embodiment of the present disclosure with a deodorization effect in storage compartments of refrigerators including air purification modules of comparative examples.

FIG. 8 is a graph comparing, a deodorization effect in a storage compartment of a refrigerator including an air purification module according to one or more embodiments of the present disclosure, with a deodorization effect in storage compartments of refrigerators including air purification modules of comparative examples. In this graph shown in FIG. 8, a curve marked by x symbols shows time-dependent concentration changes of TMA in a storage compartment of a refrigerator not including an air purification module and a curve marked by o symbols shows time-dependent concentration changes of TMA in the storage compartment of the refrigerator including the air purification module according to the one or more embodiments of the present disclosure. In the air purification module according to the embodiments of the present disclosure, the first guide has an outwardly convex surface. A curve marked by ♦ symbols shows time-dependent concentration changes of TMA by an air purification module of Comparative Example 1, in which both ends of the first guide are coplanar with each other and the first guide has a linear shape between both ends thereof. A curve marked by □ symbols shows time-dependent concentration changes of TMA by the air purification module of Comparative Example 2. The air purification modules of Comparative Examples 1 and 2 have the substantially same structure as that of the air purification module according to the embodiments of the present disclosure other than the first guide.

In this graph, the y axis indicates the ratio of a concentration after a certain period of time to an initial concentration. In this experiment, the storage compartment of the refrigerator had a volume of 400 L and was kept at 4° C. As a contaminant for confirmation of deodorization, TMA (trimethylamine) was used and an initial concentration of TMA was 5±1 ppm. As a filter in the air purification module, a photocatalyst filter having a size of 75 mm×25 mm×8 m was used. As a light source of the air purification module, two LEDs emitting UV light having a wavelength of 365 nm were used and separated from the filter by a distance of 20 mm, and had IF of 300 mA and an average radiance of 19.02 mW/cm². The blowing fan was a DFM 3510B and operated at 12 V.

Table 2 shows TMA removal efficiency of the air purification module according to the embodiments of the present disclosure and the air purification modules of Comparative Examples 1 and 2 under conditions of FIG. 8.

TABLE 2

| | TMA removal efficiency (%) | | |
| --- | --- | --- | --- |
| Time (min) | Embodiment | Comparative Example 1 | Comparative Example 2 |
| 0 | — | — | — |
| 30 | 20.8 | 15.5 | 15.5 |
| 60 | 54.2 | 46.4 | 34.5 |

TABLE 2-continued

| | TMA removal efficiency (%) | | |
|---|---|---|---|
| Time (min) | Embodiment | Comparative Example 1 | Comparative Example 2 |
| 90 | 62.5 | 57.7 | 46.4 |
| 120 | 75.0 | 73.2 | 54.2 |

Referring to FIG. 8 and Table 2, it could be seen that the refrigerator including the air purification module according to the embodiments exhibited significant reduction in concentration of a substance having an unpleasant smell, that is, TMA, over time, as compared with the refrigerator including the air purification module of Comparative Example 2 not provided with the first guide. In addition, it could be seen that the air purification module according to the embodiment has higher air purification efficiency than the air purification module of Comparative Example 2, in which the first guide has a linear shape. In particular, for an initial period of time within 2 hours after supply of TMA, the air purification module according to the embodiments exhibited much higher TMA removal efficiency than the air purification modules of Comparative Examples 1 and 2.

When the air purification module is operated in a closed space, such as a storage compartment of a refrigerator, the presence of the guide or the shape of the guide can have greater influence on removal efficiency of causative substances causing unpleasant smells in operation of the air purification module for a short period of time than in operation of the air purification module for a long period of time. Upon purification of air through circulation of the air in the closed space, removal efficiency of the causative substances may become similar due to characteristics of the closed space, regardless of the presence of the guide or the shape of the guide. However, it should be noted that the presence of the guide or the shape of the guide improves the removal efficiency of the causative substances in operation of the air purification module for a short period of time.

Whenever the door of the refrigerator is opened, new causative substances can flow into the storage compartment of the refrigerator and food, such as kimchi, can continuously discharge causative substances that cause a major smell. However, if the causative substances are present in the storage compartment without being removed for a long period of time, the causative substances can be adsorbed to the inner wall of the refrigerator or other foods, thereby causing an unpleasant smell to linger in the storage compartment of the refrigerator. Therefore, removing the causative substances within a short period of time may improve the lingering smell in the storage compartment of the refrigerator for a long period of time.

As shown in FIG. 8, it could be seen the air purification module according to the embodiments of the present disclosure could more efficiently remove TMA for a short period of time than the air purification modules of Comparative Examples 1 and 2.

Although some exemplary embodiments have been described herein, it should be understood that these exemplary embodiments are provided for illustration only and are not to be construed in any way as limiting the present disclosure, and that various modifications, changes, alterations, and equivalent exemplary embodiments can be made by those skilled in the art without departing from the spirit and scope of the disclosure. For example, although it has been described that the air outlet is provided to the exhaust cover, additionally or alternatively, the air outlet may be formed through a side wall of the casing and the like.

What is claimed is:

1. An air purification module comprising:
    a housing having an interior space defined therein and provided with an air inlet and an air outlet;
    a blowing fan disposed inside the housing to force air to flow from the air inlet to the air outlet, the blowing fan including a rotational shaft, a plurality of blades coupled to the rotational shaft, and a holding frame supporting the rotational shaft;
    a filter disposed on a flow path of the air and purifying the air;
    a guard frame disposed on the housing and configured to protect the blowing fan and block an object from entering the blowing fan;
    a sensor disposed in a region other than the flow path and configured to detect a target substance in the air;
    a driver in communication with the sensor and configured to receive, from the sensor, detection data relating to an amount of the target substance detected by the sensor and control the blowing fan based on the detection data; and
    two guide regions disposed on opposite sides of the interior space and between the blowing fan and the filter and configured to guide a flow direction of the air flowing from the air inlet to the air outlet,
    wherein each of the two guide regions includes a first sub region overlapping with at least a portion of a first region in which the blowing fan is disposed and having a first size and a second sub region disposed in a second region in which the blowing fan is not disposed and having a second size, and
    wherein the first size is different from the second size.

2. The air purification module according to claim 1, wherein the air has a flow rate of 3 m/s or less while passing through the filter.

3. The air purification module according to claim 1, wherein the filter is a photocatalyst filter.

4. The air purification module according to claim 1, wherein the two guide regions are configured to reduce a flow rate of the air between the blowing fan and the filter and guide the air such that the flow path of the air has a width gradually increasing from the blowing fan to the filter.

5. The air purification module according to claim 1, further comprising a light source unit disposed between the blowing fan and the filter and configured to emit light to the filter.

6. The air purification module according to claim 5, wherein:
    the housing comprises a ceiling and a bottom surface facing each other, and a sidewall connecting the ceiling to the bottom surface; and
    the light source unit is provided to at least one of the ceiling, the bottom surface, or the sidewall.

7. The air purification module according to claim 1, wherein the first sub region, the second sub region, or both have a curved surface or curved surfaces.

8. The air purification module according to claim 7, wherein the first sub region, the second sub region, or both are convex towards an inner surface of the housing.

9. The air purification module according to claim 1, wherein the housing comprises:
    a ceiling provided with the air inlet;
    a bottom surface facing the ceiling; and
    a sidewall connecting the ceiling to the bottom surface and provided with the air outlet.

10. The air purification module according to claim 9, wherein a lower surface of the blowing fan is tilted with respect to the bottom surface.

11. The air purification module according to claim 10, further comprising:
a second guide disposed between the bottom surface and the blowing fan and protruding from the bottom surface at an angle corresponding to an inclination of the blowing fan.

12. The air purification module according to claim 1, wherein the two guide regions extend in an upward direction and have the same height as or a greater height than an installation height of the blowing fan.

13. The air purification module according to claim 12, wherein an upper surface of the blowing fan and the two guide regions contact a ceiling of the housing.

14. The air purification module according to claim 9, wherein the blowing fan has a rotational axis tilted with respect to the bottom surface.

15. The air purification module according to claim 14, wherein the air inlet has the same diameter as or a larger diameter than a diameter of the blowing fan.

16. The air purification module according to claim 1, further comprising:
a light source unit configured to emit light to the filter; and
a light source support supporting the light source unit and connected to the two guide regions.

17. The air purification module according to claim 16, wherein the two guide regions are integrally formed with the light source support.

18. A refrigerator comprising:
a main body provided with a cooling device and a storage compartment; and
an air purification module disposed inside the storage compartment, the air purification module comprising:
a housing having an interior space defined therein and provided with an air inlet and an air outlet;
a blowing fan disposed inside the housing to force air inside the storage compartment to flow from the air inlet to the air outlet, the blowing fan including a rotational shaft, a plurality of blades coupled to the rotational shaft, and a holding frame supporting the rotational shaft;
a filter disposed on a flow path of the air and purifying the air; and
a guard frame disposed in the housing as a separate member formed separately from the housing and configured to protect the blowing fan and block an object from entering the blowing fan;
a sensor disposed in a region other than the flow path and configured to detect a target substance in the air; and
a driver in communication with the sensor and configured to receive, from the sensor, detection data relating to an amount of the target substance detected by the sensor and control the blowing fan based on the detection data; and
two guide regions disposed on opposite sides of the interior space and between the blowing fan and the filter and configured to guide a flow direction of the air flowing from the air inlet to the air outlet,
wherein each of the two guide regions includes a first sub region overlapping with at least a portion of a first region in which the blowing fan is disposed and having a first size and a second sub region disposed in a second region in which the blowing fan is not disposed and having a second size, and
wherein the first size is different from the second size.

* * * * *